United States Patent

Maruyama et al.

[11] 3,951,986
[45] Apr. 20, 1976

[54] NOVEL 2-PROPANOL DERIVATIVES AND PREPARATION THEREOF

[75] Inventors: Isamu Maruyama, Minoo; Masaru Nakao, Osaka; Kikuo Sasajima, Toyonaka; Shigeho Inaba, Takarazuka; Hisao Yamamoto, Nishinomiya, all of Japan

[73] Assignee: Sumitomo Chemical Company, Limited, Japan

[22] Filed: June 18, 1973

[21] Appl. No.: 370,693

[30] Foreign Application Priority Data

June 17, 1972   Japan.............................. 47-60587
Aug. 24, 1972   Japan.............................. 47-84866

[52] U.S. Cl..................... 260/293.73; 260/268 PH; 260/293.82; 260/293.83; 424/267
[51] Int. Cl.$^2$........................................ C07D 211/52
[58] Field of Search................. 260/268 PH, 293.83, 260/293.84, 293.73, 293.81, 293.82

[56] References Cited
UNITED STATES PATENTS

| | | | |
|---|---|---|---|
| 2,960,507 | 11/1960 | Stern et al. .................... | 260/293.84 |
| 2,978,454 | 4/1961 | Elpern .......................... | 260/293.83 |
| 3,158,616 | 11/1964 | Adickes et al. ................ | 260/293.83 |
| 3,462,444 | 8/1969 | Beckett et al................. | 260/293.84 |
| 3,840,529 | 10/1974 | Maruyama et al. ............. | 260/268 R |
| 3,845,057 | 10/1974 | Maruyama et al. .............. | 260/268 |

*Primary Examiner*—R. J. Gallagher
*Assistant Examiner*—Jose Tovar
*Attorney, Agent, or Firm*—Craig & Antonelli

[57] ABSTRACT

2-Propanol derivatives of the formula:

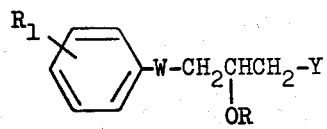

and their pharmaceutically acceptable acid addition salts, which are useful as medicaments and can be produced by reacting a compound of the formula: A-CH$_2$-Z with a compound of the formula: A'-H [wherein R is hydrogen or lower alkanoyl; R$_1$ is hydrogen, halogen, lower alkyl, lower alkoxy or trifluoromethyl; W is oxygen, sulfur, sulfinyl or sulfonyl; Y is a group of either one of the formulae:

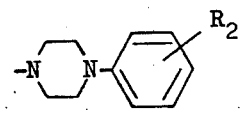

and

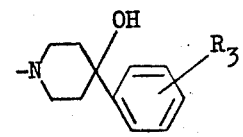

(wherein R$_2$ is hydrogen, halogen, lower alkyl or lower alkoxy and R$_3$ is hydrogen, halogen, lower alkyl, lower alkoxy or trifluoromethyl); A and A' are each a group of either one of the formulae:

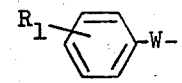

(wherein R$_1$, W and Y are each as defined above), provided that A and A' are different each other; and Z is a group of either one of the formulae:

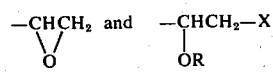

(wherein X is halogen, alkylsulfonyloxy or arylsulfonyloxy and R is as defined above)].

11 Claims, No Drawings

NOVEL 2-PROPANOL DERIVATIVES AND PREPARATION THEREOF

The present invention relates to novel 2-propanol derivatives and their pharmaceutically acceptable salts, and preparation thereof. More particularly, the present invention pertains to novel 2-propanol derivatives represented by the formula:

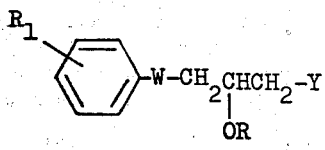

wherein R is a hydrogen atom or a lower alkanoyl group, $R_1$ is a hydrogen atom, a halogen atom, a lower alkyl group, a lower alkoxy group or a trifluoromethyl group, W is an oxygen atom, a sulfur atom, a sulfinyl group or a sulfonyl group and Y is a group of the formula:

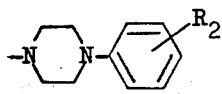

(wherein $R_2$ is a hydrogen atom, a halogen atom, a lower alkyl group or a lower alkoxy group) or a group of the formula:

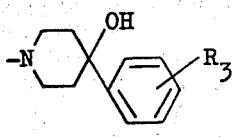

(wherein $R_3$ is a hydrogen atom, a halogen atom, a lower alkyl group, a lower alkoxy group or a trifluoromethyl group) and their pharmaceutically acceptable acid addition salts, and to processes for preparing them.

As used herein, the term "halogen" includes fluorine, chlorine, bromine and iodione. The terms "lower alkyl", "lower alkoxy" and "lower alkanoyl" mean such groups containing from one to seven carbon atoms which may be either straight or branched. Thus, the term "lower alkyl" includes methyl, ethyl, n-propyl, isopropyl, n-butyl, t-butyl, n-pentyl, n-hexyl and the like. The term "lower alkoxy" includes methoxy, ethoxy, n-propoxy, isopropoxy, n-butoxy, n-pentoxy and the like. The term "lower alkanoyl" includes acetyl, propionyl, n-butyryl, isobutyryl and the like.

The 2-propanol derivatives [I] form pharmaceutically acceptable salts with a variety of inorganic and organic acids such as sulfuric, phoshporic, hydrochloric, hydrobromic, nitric, oxalic, malonic, succinic, lactic, tartaric, maleic, fumaric, formic, acetic, salicylic and p-toluenesulfonic acids.

The 2-propanol derivatives [I] and their pharmaceutically acceptable salts have valuable pharmacological properties, in particular anti-psychotic, tranquilizing, analgesic, anti-hypertensive, anti-inflammatory and anti-arrhythmic activities, and are useful as medicaments.

The 2-propanol derivatives [I] and their pharmaceutically acceptable salts can be administered orally in conventional dosage forms such as tablet, capsule, solution, suspension, elixir or the like.

A typical tablet may be constituted from 1 to 20 percent by weight of a binder (e.g. tragacanth), from 1 to 20 percent by weight of a lubricant (e.g. talcum, magnesium stearate), an average dose of the active ingredient and q.s. 100 percent by weight of a filler (e.g. lactose). The usual oral dosage is 1 to 1000 mg per day.

Accordingly, a basic object of the present invention is to provide novel 2-propanol derivatives [I] and their pharmaceutically acceptable salts which have excellent pharmacological properties. Another object of this invention is to provide processes for producing such novel and useful 2-propanol derivatives [I] and their salts. A further object of the invention is to provide pharmaceutical compositions containing such novel and useful 2-propanol derivatives [I] or their salts. These and other objects of the invention will be apparent from the following descriptions.

According to the present invention, the novel 2-propanol derivatives [I] may be prepared by a variety of methods, of which a typical one comprises reacting a compound of the formula:

$$A-CH_2-Z \qquad [II]$$

wherein A is a group of the formula:

(wherein $R_1$ and W are each as defined above) or a group of the formula:

Y (wherein Y is as defined above) and Z is a group of the formula:

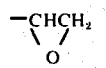

or a group of the formula:

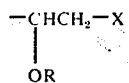

(wherein X is a halogen atom, an alkylsulfonyloxy group or an arylsulfonyloxy group and R is as defined above) with a compound of the formula:

A'-H   [III]

wherein A' is a group of the formula:

Y (wherein Y is as defined above) when A is a group of the formula:

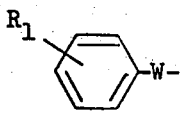

or a group of the formula:

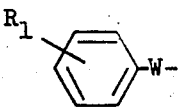

(wherein $R_1$ and W are each as defined above) when A is a group of the formula:

Y

The reaction may generally be effected in an inert solvent medium. Examples of suitable solvents are methanol, ethanol, n-propanol, isopropanol, n-butanol, benzene, toluene, xylene and dimethylformamide, and their mixture. The reaction can proceed favorably at a temperature from about room temperature to the boiling point of the solvent employed. When Z is a group of the formula:

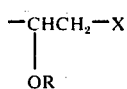

(wherein R and X are each as defined above), the reaction is preferably carried out in the presence of an acid acceptor to catch the acid which is liberated during the course of the reaction. Suitable acid acceptors include sodium carbonate, potassium carbonate, sodium bicarbonate, potassium bicarbonate, sodium hydroxide, potassium hydroxide, sodium hydride, potassium hydride, triethylamine and the like.

The 2-propanol derivatives [I], wherein R is hydrogen, may be also prepared by hydrolyzing a compound of the formula:

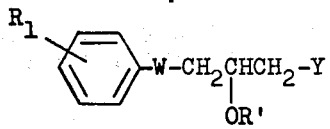

wherein $R_1$, W and Y are each as defined above and R' is a lower alkanoyl group with a saponifying agent. Suitable saponifying agents include sodium hydroxide, potassium hydroxide, sodium carbonate, potassium carbonate, sodium bicarbonate, potassium bicarbonate, hydrochloric acid, sulfuric acid and the like.

The hydrolysis is carried out at 10° to 60°C in the presence of a solvent such as water, methanol, ethanol, n-propanol, isopropanol, n-butanol or a solvent mixture thereof.

The 2-propanol derivatives [I], wherein R is lower alkanoyl, may be also prepared by acylating a compound of the formula:

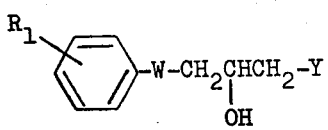

wherein $R_1$, W and Y are each as defined above with a compound of the formula:

R''-COOH   [VI]

wherein R'' is a lower alkyl group or its reactive derivative such as acid anhydride or acid halide (e.g. acid chloride).

The reaction may generally be effected in an organic solvent at a temperature from about room temperature to the boiling point of the solvent employed. Suitable solvents include benzene, toluene, xylene, pyridine, acetic acid, dimethylformamide and the like, and a solvent mixture thereof.

The 2-propanol derivatives [I], wherein R is hydrogen and W is oxygen or sulfur, may be also prepared by reduction of a compound of the formula:

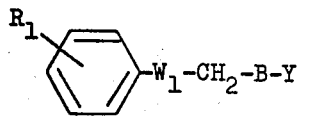

wherein B is a group of the formula:

or a group of the formula:

—COCH$_2$—

, W$_1$ is an oxygen atom or a sulfur atom and R$_1$ and Y are each as defined above.

For the reduction, there may be adopted various procedures such as reduction using a reducing agent (e.g. sodium in an alcoholic solvent, lithium aluminum hydride, sodium borohydride) or catalytic reduction. The reaction is usually carried out in the presence of a solvent or solvent mixture at a wide range of temperatures such as a cooling temperature, room temperature or an elevated temperature. The choice of solvent depends on the reducing agent employed, and examples of the solvent are water, ethanol, ether, tetrahydrofuran, dioxane, N-ethylmorpholine and the like.

The 2-propanol derivatives [I], wherein W is sulfinyl or sulfonyl, may be produced by treating the corresponding compounds wherein W is sulfur with an oxidizing agent. Examples of the oxidizing agent are chromic acid, nitric acid, hydrogen peroxide, organic peracids (e.g. performic acid, peracetic acid, perbenzoic acid, m-chloroperbenzoic acid), alkali periodates (e.g. sodium periodate, potassium periodate), alkali persulfates (e.g. sodium persulfate, potassium persulfate), selenium dioxide, lead tetracetate, manganese dioxide, ruthenium tetroxide, etc.

In general, the reaction is advantageously effected in the presence of a solvent. The choice of solvent depends on the oxidizing agent employed, and examples of the solvent are water, chloroform, carbon tetrachloride, acetone, acetic acid, formic acid, sulfuric acid, pyridine, dioxane, benzene, toluene, ether ethyl acetate, methanol, ethanol and the like, and a mixture thereof. The reaction temperature varies depending on the oxidizing agent employed. The reaction proceeds readily at room temperature, but a higher or lower temperature, for example, 0° to about 100°C or the boiling point of the solvent employed may be adopted. A preferable temperature range is from 10° to 60°C.

The 2-propanol derivatives [I], wherein Y is a group of the formula:

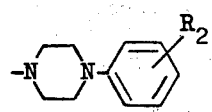

(wherein R$_2$ is as defined above), can also be prepared by reacting a compound of the fomula:

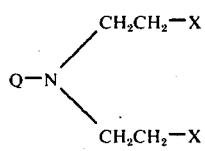 [VIII]

wherein Q is a group of the formula:

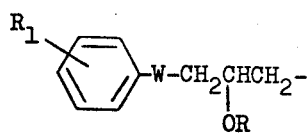

(wherein R, R$_1$ and W are each as defined above) or a group of the formula:

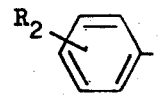

(wherein R$_2$ is as defined above) and X is as defined above with a compound of the formula:

Q'-NH$_2$ [IX]

wherein Q' is a group of the formula:

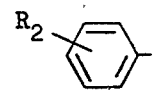

(wherein R$_2$ is as defined above) when Q is a group of the formula:

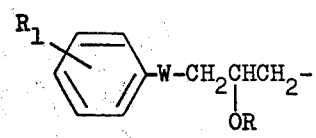

or a group of the formula:

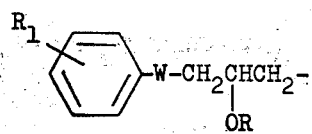

(wherein R, R$_1$ and W are each as defined above) when Q is a group of the formula:

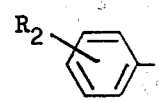

The reaction may be effected in the presence or absence of an acid acceptor (e.g. sodium carbonate, potassium carbonate, sodium bicarbonate, potassium bicarbonate, sodium hydroxide, potassium hydroxide, triethylamine) and also in the presence or absence of a solvent such as an alcohol (e.g. methanol, ethanol, n-propanol, isopropanol, n-butanol, cyclohexanol), an aromatic hydrocarbon (e.g. benzene, toluene, xylene) or a mixture thereof. The reaction temperature may be from about room temperature to the boiling point of the solvent employed.

Among the significances of the symbol X as mentioned above, the halogen atom includes chlorine and bromine, the alkylsulfonyloxy group includes methylsulfonyloxy and ethylsulfonyloxy and the arylsulfonyloxy group includes p-toluenesulfonyloxy and β-naphthalenesulfonyloxy.

The starting compounds used in the processes as described above can be easily produced, for instance, as shown in the following scheme:
(1)
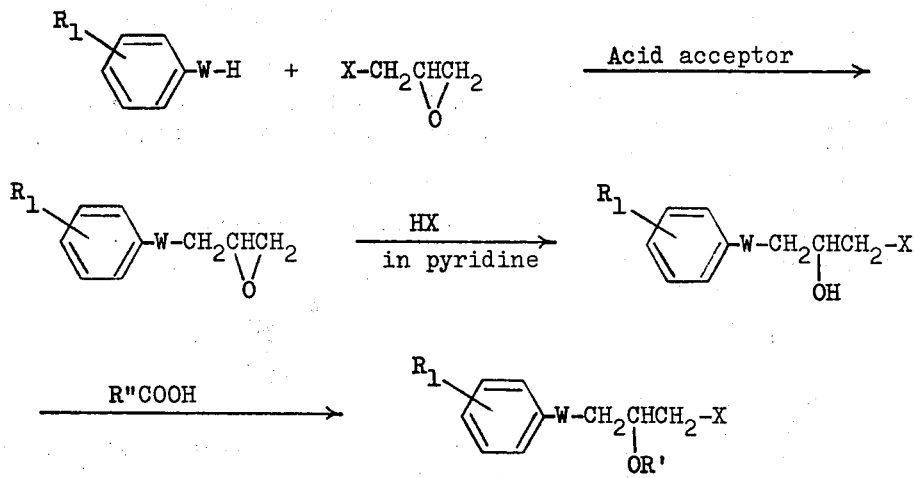
(2)
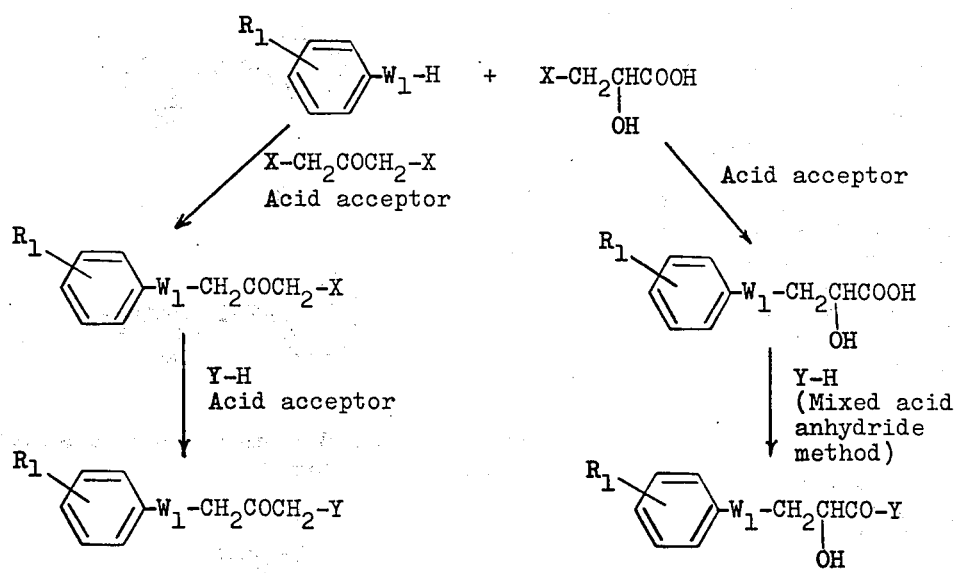
(3)
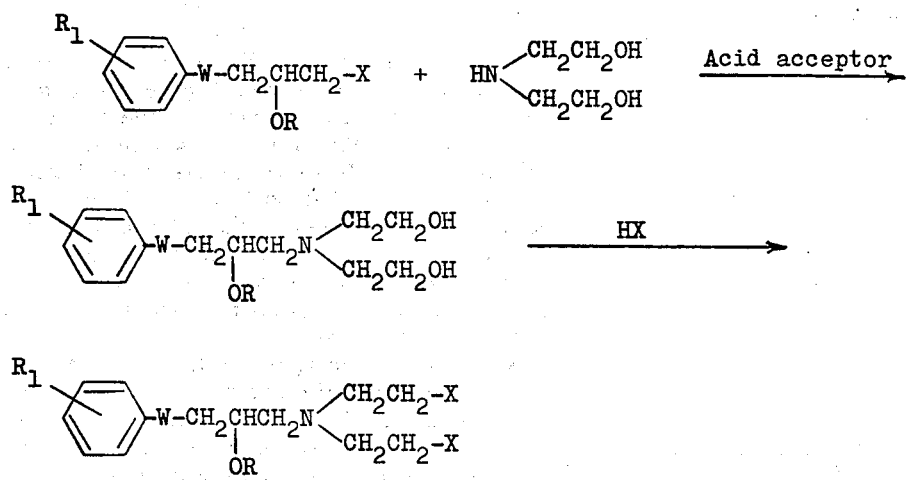

(4)

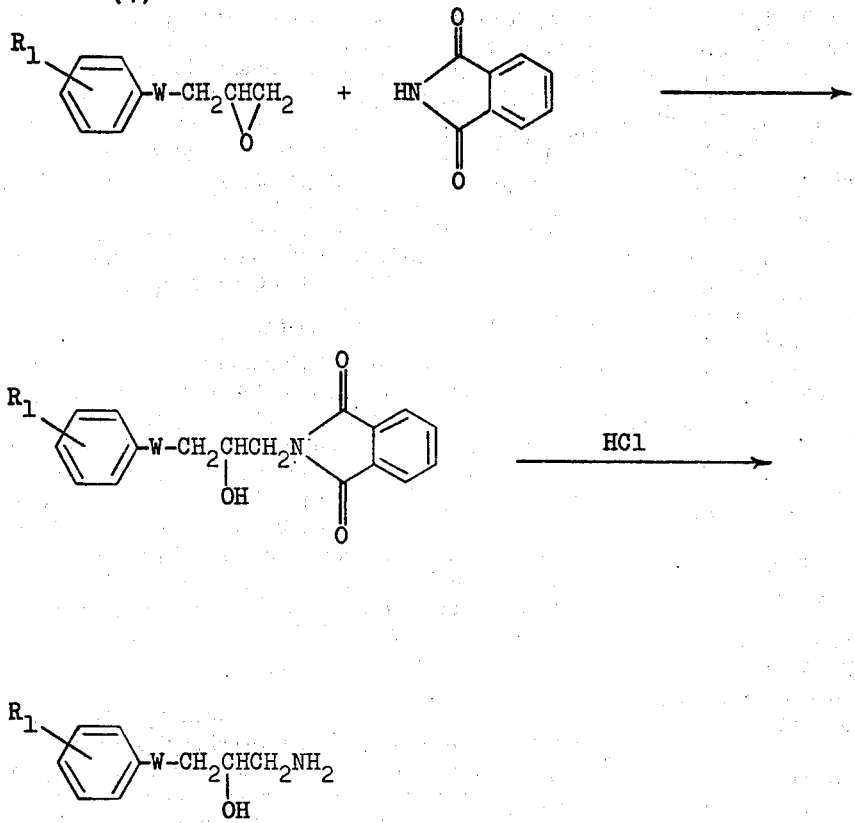

wherein R, R', R'', R₁, W, W₁, Y and X are each as defined above.

The thus obtained 2-propanol derivative [I] in free base can be converted into the acid addition salt by interaction of the base with an acid. In like manner, the free base can be regenerated from the acid addition salt by treating the salt with a strong base such as alkali metal hydroxide, alkali metal carbonate and alkali metal bicarbonate. The base thus regenerated can then be interacted with the same or a different acid to give the corresponding acid addition salt. Thus, the novel bases and all of their acid addition salts are readily interconvertible.

The present invention is further disclosed in the following examples of more preferred embodiments thereof, which are presented for the purpose of illustration and it is not intended to limit the scope of the invention.

EXAMPLE 1

A mixture of 2.53 g of 1,2-epoxy-3-(p-fluorophenoxy)-propane, 2.88 g of 1-(o-methoxyphenyl)piperazine and 50 ml of ethanol is refluxed for 5 hours. The reaction mixture is concentrated under reduced pressure. Then, the residue is added to water and extracted with benzene. The organic layer is dried over sodium sulfate and evaporated under reduced pressure. The oily residue is dissolved in ether and treated with ethanolic hydrogen chloride under cooling. The precipitate is collected by filtration and dried to give 1-[2-hydroxy-3-(p-fluorophenoxy)propyl]-4-(o-methoxyphenyl)piperazine dihydrochloride. M.P. 195 to 200°C (decomp.). Recrystallization from methanol gives white crystals, M.P. 199° to 200°C (decomp.).

The following compounds are obtained in the same manner as in Example 1:

1-[2-Hydroxy-3-(p-fluorophenoxy)propyl]-4-(o-ethoxyphenyl)piperazine, M.P. 112° to 112.5°C;

1-[2-Hydroxy-3-(p-fluorophenoxy)propyl]-4-(o-tolyl)piperazine hydrochloride, M.P. 183° to 184°C;

1-[2-Hydroxy-3-(p-fluorophenoxy)propyl]-4-(o-chlorophenyl)piperazine hydrochloride, M.P. 170° to 171°C;

1-[2-Hydroxy-3-(m-trifluorophenoxy)propyl]-4-(o-methoxyphenyl)piperazine dihydrochloride, M.P. 190° to 196°C (decomp.);

1-[2-Hydroxy-3-(p-fluorophenylthio)propyl]-4-(o-methoxyphenyl)piperazine dihydrochloride, M.P. 216° to 221°C (decomp.);

1-[2-Hydroxy-3-(p-fluorophenylthio)propyl]-4-(o-chlorophenyl)piperazine hydrochloride, M.P. 161.5° to 162.5°C;

1-[2-Hydroxy-3-(p-tolylthio)propyl]-4-(o-methoxyphenyl)piperazine, M.P. 86° to 87°C;

1-[2-Hydroxy-3-(p-fluorophenoxy)propyl]-4-(p-chlorophenyl)-4-hydroxypiperidine, M.P. 107° to 108°C;

1-[2-Hydroxy-3-(p-fluorophenoxy)propyl]-4-hydroxy-4-(m-trifluoromethylphenyl)piperidine, M.P.

122° to 123°C;

1-[2-Hydroxy-3-(p-fluorophenoxy)propyl]-4-(p-fluorophenyl)-4-hydroxypiperidine, M.P. 116° to 117°C;

1-[2-Hydroxy-3-phenoxypropyl]-4-(p-chlorophenyl)-4-hydroxypiperidine, M.P. 131° to 131.5°C;

1-[2-Hydroxy-3-(m-fluorophenoxy)propyl]-4-(p-chlorophenyl)-4-hydroxypiperidine, M.P. 108° to 109°C;

1-[2-Hydroxy-3-(o-fluorophenoxy)propyl]-4-(p-chlorophenyl)-4-hydroxypiperidine, M.P. 129° to 130°C;

1-[2-Hydroxy-3-(p-methoxyphenoxy)propyl]-4-(p-chlorophenyl)-4-hydroxypiperidine, M.P. 104° to 104.5°C;

1-[2-Hydroxy-3-(p-ethoxyphenoxy)propyl]-4-(p-chlorophenyl)-4-hydroxypiperidine, M.P. 112° to 112.5°C;

1-[2-Hydroxy-3-(o-ethoxyphenoxy)propyl]-4-(p-chlorophenyl)-4-hydroxypiperidine, M.P. 82° to 82.5°C;

1-[2-Hydroxy-3-(p-chlorophenoxy)propyl]-4-(p-chlorophenyl)-4-hydroxypiperidine, M.P. 146° to 147°C;

1-[2-Hydroxy-3-(p-tolyloxy)propyl]-4-(p-chlorophenyl)-4-hydroxypiperidine, M.P. 131° to 131.5°C;

1-[2-Hydroxy-3-(p-fluorophenylthio)propyl]-4-(p-chlorophenyl)-4-hydroxypiperidine, M.P. 103° to 105°C;

1-[2-Hydroxy-3-(p-fluorophenylthio)propyl]-4-hydroxy-4-(m-trifluoromethylphenyl)piperidine, M.P. 85° to 85.5°C, etc.

EXAMPLE 2

A mixture of 2 g of 1-[2-acetyloxy-3-(p-fluorophenoxy)propyl]-4-(o-methoxyphenyl)piperazine, 1.1 g of potassium hydroxide, 5 ml of water and 20 ml of ethanol is stirred at room temperature for 1 hour. The reaction mixture is poured into water and extracted with benzene. The organic layer is washed with water, dried over sodium sulfate and evaporated under reduced pressure. The oily residue is dissolved in ether and treated with ethanolic hydrogen chloride under cooling. The precipitate is collected by filtration and dried to give 1-[2-hydroxy-3-(p-fluorophenoxy)propyl]-4-(o-methoxyphenyl)piperazine dihydrochloride, M.P. 196° to 198°C (decomp.). Recrystallization from ethanol gives white crystals, M.P. 199° to 200°C (decomp.).

EXAMPLE 3

A mixture of 0.65 g of 1-[2-hydroxy-3-(p-fluorophenoxy)propyl]-4-(o-methoxyphenyl)piperazine, 1.8 g of acetic anhydride and 15 ml of acetic acid is heated at 80°C for 2 hours. After cooling, the reaction mixture is diluted with water, made alkaline with aqueous ammonia and extracted with benzene. The organic layer is washed with water, dried over sodium sulfate and evaporated under reduced pressure. The oily residue is dissolved in ether and cooled. The precipitate formed is collected by filtration and dried to give 1-[2-acetyloxy-3-(p-fluorophenoxy)propyl]-4-(o-methoxyphenyl)piperazine, M.P. 68° to 72°C. Recrystallization from cyclohexane-hexane gives white crystals, M.P. 71.5° to 72°C.

The following compounds are obtained in the same manner as in Example 3:

1-[2-Acetyloxy-3-(p-fluorophenylthio)propyl]-4-(o-methoxyphenyl)piperazine dihydrochloride, M.P. 184.5° to 186°C (decomp.).

1-[2-Acetyloxy-3-(p-fluorophenylthio)propyl]-4-(o-chlorophenyl)piperazine oxalate, M.P. 124.5° to 125°C;

1-[2-Acetyloxy-3-(p-fluorophenoxy)propyl]-4-(p-chlorophenyl)-4-hydroxypiperidine hydrochloride, M.P. 208° to 209°C (decomp.).

1-[2-Acetyloxy-3-(p-fluorophenoxy)propyl]-4-hydroxy-4-(m-trifluoromethylphenyl)piperidine hydrochloride, M.P. 209° to 209.5°C (decomp.).

EXAMPLE 4

A mixture of 1.9 g of 1-[2-oxo-3-(p-fluorophenoxy)propyl]-4-(p-chlorophenyl)-4-hydroxypiperidine, 0.38 g of sodium borohydride and 20 ml of methanol is stirred at room temperature for 3 hours. The resulting mixture is diluted with water and extracted with chloroform. The organic layer is dried over sodium sulfate and evaporated under reduced pressure to give 1-[2-hydroxy-3-(p-fluorophenoxy)propyl]-4-(p-chlorophenyl)-4-hydroxypiperidine, M.P. 103° to 105°C. Recrystallization from benzene-cyclohexane gives white crystals, M.P. 107° to 108°C.

EXAMPLE 5

To a solution of 1.85 g of 1-[2-hydroxy-3-(p-fluorophenylthio)propyl]-4-(o-methoxyphenyl)piperazine in 20 ml of glacial acetic acid is added dropwise 1.2 g of 35 % aqueous hydrogen peroxide solution under cooling, and the mixture is stirred at a temperature of 20° to 30°C for 1 hour. The reaction mixture is poured into water, neutralized with aqueous ammonia and extracted with benzene. The organic layer is washed with water, dried over sodium sulfate and evaporated under reduced pressure. The oily residue is crystallized by cooling to give 1-[2-hydroxy-3-(p-fluorophenylsulfinyl)propyl]-4-(o-methoxyphenyl)piperazine, M.P. 164° to 165°C. Recrystallization from benzene gives white crystals, M.P. 167.5° to 168.5°C.

The following compounds are obtained in the same manner as in Example 5:

1-[2-Hydroxy-3-(p-fluorophenylsulfinyl)propyl]4-(o-chlorophenyl)piperazine, M.P. 145° to 146°C;

1-[2-Hydroxy-3-(phenylsulfinyl)propyl]-4-(o-methoxyphenyl)piperazine, M.P. 166° to 167°C;

1-[2-Hydroxy-3-(p-tolylsulfinyl)propyl]-4-(o-methoxyphenyl)piperazine, M.P. 149° to 150°C;

1-[2-Acetyloxy-3-(p-fluorophenylsulfinyl)propyl]-4-(o-methoxyphenyl)piperazine, M.P. 134° to 135°C;

1-[2-Hydroxy-3-(p-fluorophenylsulfinyl)propyl]-4-hydroxy-4-(m-trifluoromethylphenyl)piperidine, M.P. 131° to 132°C, etc.

EXAMPLE 6

A mixture of 3.7 g of 1-amino-2-hydroxy-3-(p-fluorophenoxy)propane, 8.3 g of N,N-bis(β-bromoethyl)-o-anisidine hydrobromide and 30 ml of butanol is heated under reflux for 10 hours. The mixture is then cooled to about 50°C, and 1 g of sodium carbonate is added thereto. The mixture is again heated under reflux for 10 hours. After completion of the reaction, the reaction mixture is concentrated to about half the original volume under reduced pressure. After cooling, the precipitate is collected by filtration, suspended in water and made alkaline with a 30 % aqueous sodium hydroxide solution. The separated oily substance is extracted with benzene. The organic layer is washed with water, dried over anhydrous sodium sulfate and evaporated under reduced pressure. The oily residue is dissolved in ether and treated with ethanolic hydrogen chloride under cooling. The precipitate is collected by filtration and dried to give 1-[2-hydroxy-3-(p-fluorophenoxy)propyl]-4-(o-methoxyphenyl)piperazine dihydrochloride, M.P. 195° to 198°C (decomp.).

What is claimed is:

1. 1-[2-hydroxy-3-(p-fluorophenoxy)propyl]-4-(p-chloro-phenyl)-4-hydroxypiperidine.

2. 1-[2-Hydroxy-3-(p-fluorophenoxy)propyl]-4-(p-chlorophenyl)-4-hydroxypiperidine, and its pharmaceutically acceptable salts.

3. 1-[2-Hydroxy-3-(p-fluorophenoxy)propyl]-4-(m-trifluoromethylphenyl)-4-hydroxypiperidine, and its pharmaceutically acceptable salts.

4. 1-[2-Hydroxy-3-(p-chlorophenoxy)propyl]-4-(p-chlorophenyl)-4-hydroxypiperidine, and its pharmaceutically acceptable salts.

5. 1-[2-Hydroxy-3-(p-methoxyphenoxy)propyl]-4-(p-chlorophenyl)-4-hydroxypiperidine, and its pharmaceutically acceptable salts.

6. 1-[2-Hydroxy-3-(o-ethoxyphenoxy)propyl]-4-(p-chlorophenyl)-4-hydroxypiperidine, and its pharmaceutically acceptable salts.

7. 1-[2-Hydroxy-3-(p-tolyloxy)propyl]-4-(p-chlorophenyl)-4-hydroxypiperidine, and its pharmaceutically acceptable salts.

8. 1-[2-Hydroxy-3-(p-fluorophenylthio)propyl]-4-(p-chlorophenyl)-4-hydroxypiperidine, and its pharmaceutically acceptable salts.

9. 1-[2-Acetyloxy-3-(p-fluorophenoxy)propyl]-4-(m-trifluoromethylphenyl)-4-hydroxypiperidine, and its pharmaceutically acceptable salts.

10. 1-[2-Hydroxy-3-(p-fluorophenylsulfinyl)propyl]-4-(m-trifluoromethylphenyl)-4-hydroxypiperidine, and its parmaceutically acceptable salts.

11. 1-[2-Hydroxy-3-(m-fluorophenoxy)propyl]-4-(p-chlorophenyl)-4-Hydroxypiperidine, and its pharmaceutically acceptable salts.

* * * * *